United States Patent [19]

Györgydeák et al.

[11] Patent Number: 4,775,675
[45] Date of Patent: Oct. 4, 1988

[54] THIAZOLIDINECARBOXYLIC ACID DERIVATIVES AND TREATMENT OF LIVER DISEASES THEREWITH

[75] Inventors: Zoltán Györgydeák; István Kovács; Rezsö Bognár; Géza Horváth; János Bálint; Attila Jakab; Judit Krusper née Hám, all of Debrecen; Károly Lapis; Béla Szende, both of Budapest; Ferenc Pusztai, Debrecen; Mariann Fekete née Huszka, Debrecen; Sándor Jancsó, Debrecen; Terézia Mile, Debrecen; Ildikó Mihók née Borbély, Debrecen; András Jenei, Budapest, all of Hungary

[73] Assignee: Biogal Gyógyszergyár, Drebrecen, Hungary

[21] Appl. No.: 874,111

[22] Filed: Jun. 13, 1986

[30] Foreign Application Priority Data

Jun. 18, 1985 [HU] Hungary .................. 2388/85

[51] Int. Cl.$^4$ .................. C07D 277/04; C07D 217/00; C07D 215/12; C07D 409/00
[52] U.S. Cl. .................. 514/307; 548/201; 546/147; 546/174; 546/280; 514/365; 514/369; 514/314; 514/342
[58] Field of Search .................. 548/201; 546/147, 174, 546/280; 514/365, 369, 307, 314, 342

[56] References Cited

U.S. PATENT DOCUMENTS

3,947,464  3/1976  Asinger et al. .................. 548/188

FOREIGN PATENT DOCUMENTS

| 738520 | 9/1969 | Belgium | 548/188 |
| 751482 | 6/1970 | Belgium | 548/188 |
| 2116629 | 4/1971 | Fed. Rep. of Germany | 548/188 |
| 2614798 | 4/1976 | Fed. Rep. of Germany | 548/188 |
| 923562 | 3/1965 | France | 548/188 |

OTHER PUBLICATIONS

Asinger, et al., Montushefte für Chemie, 114, 47–63 (1983).
Nagasawa, et al.,–Chem. Abs. 95:219690v.
Schubert, J. Biol. Chem. 114, 341 (1936).

*Primary Examiner*—Alan L. Rotman
*Assistant Examiner*—Robert C. Whittenbaugh
*Attorney, Agent, or Firm*—Schweitzer & Cornman

[57] ABSTRACT

The invention relates to novel thiazolidine-4(S)-carboxylic acid derivatives of the general formula (I)

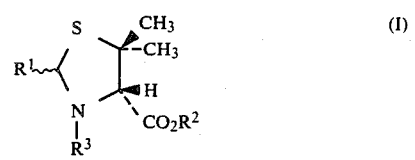

wherein
$R^1$ stands for an optionally substituted furyl, pyrrolyl, thienyl, benzofuryl, benzopyrrolyl, benzothienyl, phenyl, pyridyl, quinolinyl, isoquinolinyl or indanyl group or a $C_{1-4}$ alkyl or $C_{2-4}$ alkenyl group optionally substituted by a hydroxyl, carboxyl or halogen fenoxy group,
stands for hydrogen, an alkaline metal or an alkaline earth metal atom or an optionally substituted $C_{1-4}$ alkyl group or aryl group;
$R^3$ represents hydrogen or an optionally substituted $C_{1-4}$ alkyl or acyl group or aryl group
as well as their salts.

Further on, the invention relates to pharmaceutical preparations containing these compounds and to a process for preparing these compounds and preparations.

The compounds of the invention are useful for treating or preventing liver damages of either natural or experimental origin.

1 Claim, No Drawings

THIAZOLIDINECARBOXYLIC ACID DERIVATIVES AND TREATMENT OF LIVER DISEASES THEREWITH

The invention relates to novel thiazolidinecarboxylic acid derivatives. More particularly, the invention relates to new thiazolidine-4(S)-carboxylic acid derivatives of the general formula (I),

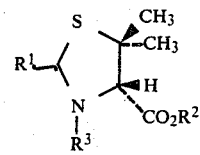

wherein
$R^1$ stands for an optionally substituted furyl, pyrrolyl, thienyl, benzofuryl, benzopyrrolyl, benzothienyl, phenyl, pyridyl, quinolinyl, isoquinolinyl or indanyl group or a $C_{1-4}$ alkyl or $C_{2-4}$ alkenyl group optionally substituted by a hydroxyl, carboxyl or halogen fenoxy group, $R^2$ stands for hydrogen, an alkaline metal or an alkaline earth metal atom or an optionally substituted $C_{1-4}$ alkyl group or aryl group;

$R^3$ represents hydrogen or an optionally substituted $C_{1-4}$ alkyl or acyl group or aryl group as well as their salts.

When $R^1$ means a five-membered ring containing one heteroatom, then the compounds are represented by the general formula (II)

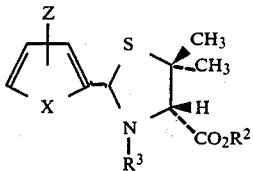

wherein
X stands for oxygen, sulphur, or nitrogen; and
Z stands for hydrogen, halogen or an optionally substituted $C_{1-4}$ alkyl or $C_{1-4}$ alkoxy group or a nitro, mercapto, amino, hydroxyl, carboxyl, or acyl group.

When $R^1$ means a group containing a condensed ring system, then the compounds are represented by the general formula (III)

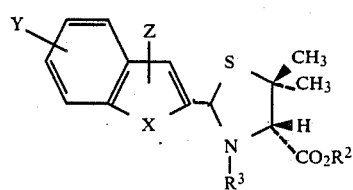

or

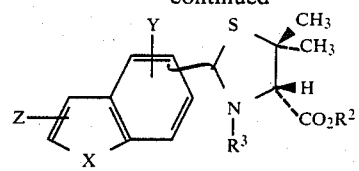

wherein
A stands for hydrogen, halogen, a $C_{1-4}$ alkyl or acyl group optionally substituted by a hydroxyl group; or a mercapto, nitro, carboxyl, hydroxyl or acyloxy group;
X is as defined above and may also stand for carbon; and
n means 1, 2 or 3.

When $R^1$ means a ring consisting of six carbon atoms, then the compounds are represented by the general formula (V)

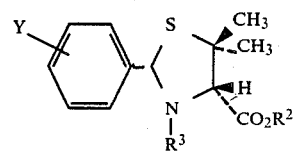

wherein $R^2$, $R^3$, Y and n are as defined above.

When $R^1$ means a six-membered ring containing one nitrogen atom, then this ring can be bound through its $C_2$-, $C_3$- or $C_4$-position to the 5,5-dimethylthiazolidine-4(S)-carboxylic acid moiety as shown by the general formula (Va)

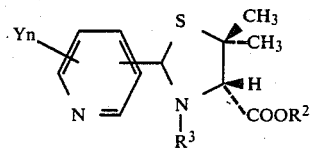

wherein $R^2$, $R^3$, Y and n are as defined above.

According to an other aspect of the invention, there is provided a process for the preparation of the new compounds of the general formula (I) and salts thereof.

The process of the invention is useful for the preparation of thiazolidine-4(S)-carboxylic acid derivatives which can be utilized for treating or preventing liver damages of either natural or experimental origin.

Among thiazolidine-4-carboxylic acids, several biologically active substances have been described. Some of these compounds are known as liver protecting agent.

In the French patent specification No. 3,184M a novel thiazolidine-4-carboxylic acid is reported which possesses liver protecting, liver restoring (liver regenerating), antinecrotic and proteinotropic effects.

According to the German patent specification No. 2 116 629, thiazolidine-4-carboxylic acid derivatives are prepared by reacting a thiazolidine-4-carboxylic acid with an acid anhydride or by reacting cysteine hydrochloride with pyruvic acid (to give 2-methylthiazolidine-2,4-dicarboxylic acid) or with 3-formylphenoxyacetic acid [to give 2-(2-phenoxyacetyl)-thiazolidine-4-carboxylic acid] or with other organic acids. These compounds show a liver protecting effect.

3-(4-Chlorophenoxy-isobutyryl)-5,5-dimethyl-thiazolidine-4-carboxylic acid reported in the German patent specification No. 2 446 100 shows an anti-hyperlipaemic effect.

In the German patent specification No. 2 614 798, 2-methylamino-5-(5-nitro-2-furfurylidene)-thiazolin-4-one and 2-imino-3-methyl-5-(5-nitrofurfurylidene)-thiazolidin-4-one compounds are described which show a synergistic action on using in combination and are capable of preventing the mucus formation during the working-up process in the paper industry.

In the Belgian patent specification No. 751,482, thiazolidine-2,4-dicarboxylic acids and derivatives are described which possess liver protecting, liver restoring (regenerating) and detosicating effects. Thiazolidine-2,4-dicarboxylic acid is prepared from cysteine and sodium acetate in the presence of triethylamine.

F. Asinger and coworkers reported the preparation of 5,5-dimethyl-thiazolidine-4(R,S)-carboxylic acids and their derivatives [Monatshefte für Chemie 114, 47 (1983)]. According to this paper, D,L-penicillamine hydrochloride is condensed with various aldehydes or ketone to obtain the aimed compounds as racemates containing two chiral centres in the form of hydrochlorides or free bases. The biological activity of the thus-prepared compounds have not been investigated; the mechanism of the condensation was the object of this study.

Penicillamine is an aminoacid containing several functional groups, a characteristic reaction of which is the condensation with compounds containing a carbonyl group followed by cyclisation. As a result of this reaction, 5,5-dimethylthiazolidine-4-carboxylic acids are formed which are substituted by various groups in the 2-position. Esters, amides, S- as well as N-derivatives may be obtained from the thus-prepared carboxylic acids by further chemical transformations.

It is known from the prior art that a part of thiazolidinecarboxylic acid derivatives show a liver protecting effect. According to the present knowledge, this liver protecting effect appears in that thiazolidinecarboxylic acids play a role in such processes through which several enzymes of the organism and, within the organism, several enzymes of the liver are re-activated in such a way that the accumulated disulphide moieties are re-transformed to free thiol groups.

According to several known experiments, thiazolidine-4-carboxylic acids are prepared from D,L-cysteine or from D,L-penicillamine as starting materials. Finally, both reaction types result in racemic compounds containing two centres of asymmetry, i.e. in the formation of four isomers with various steric (spatial) structures in each reaction. The biological activity of the molecules having various spatial structures is different, biologically inactive forms are also found.

With the purpose to exclude previously the inactive and slightly active forms on the basis of knowledge of the activities, it was concluded that one of the centres of asymmetry can be fixed and thus, the number of the possible isomers can be diminished to the half by using one of the optical isomers as starting material.

Accordingly, in addition to the preparation of the novel and pharmacologically active molecules, a particular attention has been paid to the formation (development) of the spatial structure of the thiazolidine-4-carboxylic acid molecules resulting from the condensation.

Oppositely to the previous experiments, D-penicillamine has been used as starting material within our investigations. Thus, the number of the possible isomers has been decreased to its half, i.e. the occurrence of the cis[2(S), 4(S)] and trans[(R), 4(S)] diastereomers should only be considered.

Based on these fact, there is provided a process for preparing the compounds of the general formula (I), wherein $R^1$, $R^2$ and $R^3$ are the same as defined above, and their salts, which comprises reacting a compound of the general formula (X)

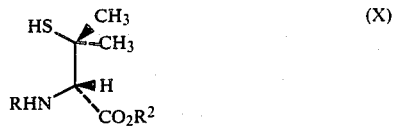

wherein R stands for hydrogen or an acyl group, with an aldehyde of the general formula (VI), (VII), (VIII(, (IX), (IXa), (XI) or (XIa)

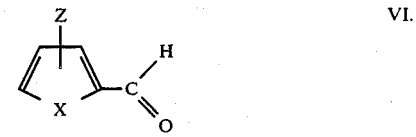

VI.

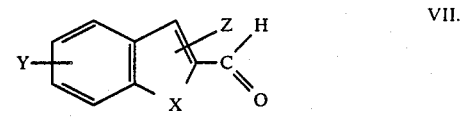

VII.

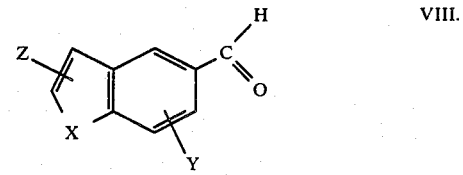

VIII.

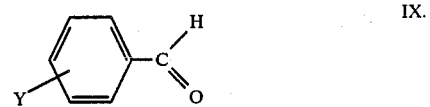

IX.

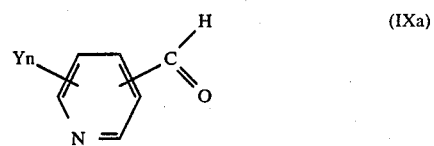

(IXa)

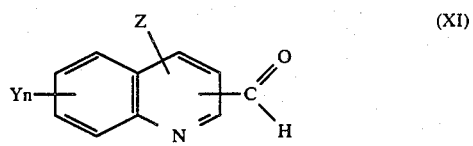

(XI)

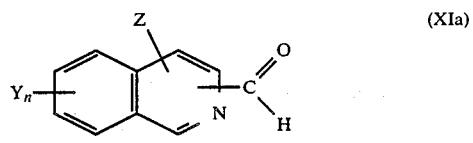

(XIa)

wherein
X stands for oxygen, sulphur, or nitrogen and in the formula (VII) and (VIII) X can also represent a carbonatom,
Z stands for hydrogen, halogen or an optionally substituted $C_{1-4}$ alkyl or $C_{1-4}$ alkoxy group or a nitro, mercapto, amino, hydroxyl, carboxyl or acyl group; and Y stands for hydrogen, halogen, a $C_{1-4}$ alkyl or acyl group optionally substituted by a hydroxyl group; or a mercapto, nitro, carboxyl, hydroxyl or acyloxy group; and n means 1, 2 or 3, and, if desired transforming a thus-obtained compound of the general formula (I), wherein $R^2$ means hydrogen, to the corresponding alkaline metal or alkaline earth metal salt thereof, or esterifying a thus-obtained compound of the general formula (I), wherein $R^2$ represents hydrogen or one equivalent of an alkaline metal or an alkaline earth metal and/or reacting a thus-obtained compound of the general formula (I), wherein $R^3$ stands for hydrogen, with an acid anhydride or an acyl halide to give the corresponding N-acyl derivative and acylating simultaneously a hydroxyl group being optionally bound to the $R^1$ substituent.

Thus, the novel compounds are condensation products formed from the compounds of the general formula (X), having D-configuration in their chirality centre, with the aldehydes of the general formulae (VI), (VII), (VIII), (IX), (IXa), (XI) or (XIa) as well as their 3-acyl and 4-ester derivatives.

The process of the invention is illustrated in detail by the Examples.

Examples 1 to 22 illustrate the condensation of the compounds of the general formula (X) with the aldehydes of the general formulae (VI), (VII), (VIII), (IX), (IXa), (XI) or (XIa), respectively to give a 5,5-dimethyl-2-substituted-thiazolidine-4(S)-carboxylic acid or a 3-acyl-5,5-dimethyl-2-substituted-thiazolidine-4(S)-carboxylic acid.

According to a preferred embodiment of the process of the invention, a compound of the general formula (X) (R=H) is dissolved in water and/or in a water-miscible organic solvent, whereupon a compound of the general formula (VI), (VII), (VIII), (IX), (IXa), (XI) or (XIa), respectively, is portionwise added while stirring. The mixture is stirred for additional 0.1 to 24 hours at a temperature between 0° C. and 45° C., while the aimed product crystallizes out. The aimed product is isolated from the mixture by filtration or evaporation.

When R in the compound of the general formula (X) stands for an acyl group, then the compound of the formula (X) is dissolved in an apolar solvent containing an acidic catalyst and a compound of the general formula (VI), (VII), (VIII), (IX), (IXa), (XI) or (XIa), respectively is portionwise added. The mixture is stirred for 1 to 180 minutes at room temperature, whilst the aimed product precipitates in a crystalline form. The product is separated from the mixture by filtration.

According to an other preferred embodiment of the process of the invention which is illustrated in Examples 23 to 30, a 5,5-dimethyl-2-substituted-thiazolidine-4(S)-carboxylic acid is reacted with an acid anhydride or acyl halide to give the corresponding 3-acyl-5,5-dimethyl-2(S)-substituted-thiazolidine-4(S)-carboxylic acid.

In this embodiment of the process of the invention, a compound of the general formula (I), wherein $R^3$ stands for hydrogen, is dissolved in water or in an organic solvent and an acid anhydride or acyl halide is portionwise added to the above solution while constant stirring. On using water as solvent, the reaction is carried out at a temperature of 30° to 100° C., whereupon on cooling the aimed product crystallizes out from the mixture. When an organic solvent, preferably pyridine is used, then the reaction is performed at or lower than room temperature and the aimed product is obtained by evaporation.

In the process described in Examle 32, a 5,5-dimethyl-2(S)-substituted-thiazolidine-4(S)-carboxylic acid alkyl ester is prepared by the reaction of the appropriate carboxylic acid with diazomethane.

The esters are prepared in such a way that a compound of the general formula (I), wherein $R^2$ stands for hydrogen, an alkaline metal or an alkaline earth metal atom, is dissolved in a polar solvent, suitably in alcohol, whereupon an alkylating agent is added under cooling. The aimed product is obtained by evaporation.

In general, the isomers obtained from the reactions cannot be distinguished by thin layer chromatography. When the development of the mixture of isomers is carried out on Kieselgel 60 $F_{254}$ sheet by using a system containing a little amount of an organic acid, then a single compact spot is obtained.

The NMR spectra were taken in all cases in dimethylsulphoxide.

The invention is illustrated in detail by the aid of the following non-limiting Examples.

EXAMPLE 1

5,5-Dimethyl-2-(5-nitro-2-furyl)-thiazolidine-4(S)-carboxylic acid

A solution containing 12.5 g (0.1 mole) of 5-nitrofurfural in 60 ml of methanol is dropped to the solution containing 15 g (0.1 mole) of D-penicillamine in 190 ml of ion-free water under continuous stirring within 10 to 12 minutes. The mixture is stirred for additional 1 hour, whilst a beige-coloured product starts to precipitate. The crystals are filtered, washed with 20 ml of ion-free water and dried on the air to give 23.9 (87.7%) of a crude product which is dissolved in 26 ml of hot methanol and 8 to 10 ml of ion-free water are dropped to this solution until the beginning of crystal precipitation. For completion of the crystallization, the mixture is kept in the refrigarator, then filtered, washed with 15 ml of 50% methanol and dried at a temperature not higher than 55° C. to give the title compound in a yield of 19.7 g (72.3%), m.p.: 147°–148° C.; $[\alpha]_D^{20} = -159°$ (c=0.829, dimethylsulphoxide).

Analysis:

(Molecular weight 272.3): Calculated: N %=10.29, S %=11.78%; Found: N %=10.14, S %=11.78%.

IR ($cm^{-1}$): 3304 (NH, 1725 (CO), 2480 (indicating the zwitterionic structure).

| $^1H$—NMR ($\delta$, ppm): | 1.34 and 1.65 (C—methyl cis) |
|---|---|
| | 1.40 and 1.69 (C—methyl trans) |
| | 5.77 (H-2) cis isomer |
| | 3.64 (H-4) |
| | 5.71 (H-2) trans isomer |
| | 3.70 (H-4) trans isomer |

EXAMPLE 2

5,5-Dimethyl-2-(2-furyl)-thiazolidine-4(S)-carboxylic acid

A solution containing 2.48 ml of furfural and 4.27 g of D-penicillamine in 90 ml of 30% methanol is stirred for 8 hours, then evaporated to dryness. The partly crystalline residue is rubbed with ether to give the title compound, m.p.: 141°–143° C., $[\alpha]_D^{20} = +103°$ (c=0.602, dimethylsulphoxide).

Analysis:

(Molecular weight 227.3): Calculated: N %=6.16, S %=14.10; Found: N %=5.91; S %=13.69.

IR (cm$^{-1}$): 1721 (CO)

$^1$H-NMR ($\delta$, ppm): 1.22 and 1.53 (C-methyl, trans), 1.28 and 1.56 (C-methyl, cis), 3.58 (H-4) cis, 5.70 (H-2) cis, 3.60 (H-4) trans, 5.66 (H-2) trans.

EXAMPLE 3

5,5-Dimethyl-2-(2-(thienyl)-thiazolidine-4(S)-carboxylic acid 0.92 ml (1.12 g, 10 mmoles) of thiphene-2-aldehyde is added to a solution containing 1.5 g (10 mmoles) of D-penicillamine in 150 ml of methanol at room temperature under stirring, then the mixture is stirred for 48 hours and then evaporated to dryness under reduced pressure. The residue is dissolved in hot benzene while stirring and filtered. After adding petroleum ether to the filtrate, the title product crystallizes out in a yield of 1.5 g (61.6%), m.p.: 129°–131° C., $[\alpha]_D^{20} = +56°$ (c=0.549, dimethylsulphoxide).

Analysis:

(Molecular weight: 243.3): Calculated: N %=5.75, S %=26.35; Found: N %=5.31, S %=26.62.

$^1$H-NMR ($\delta$, ppm): 1.3 (s; 3H, C—CH$_3$); 1.6 (s, 3H, C—CH$_3$); 3.42 (b; NH); 3.62 (s; 1H, H$_4$); 5.9 (s; 1H, H$_2$); 6.92–7.52 (m, 4H, thiophene protons).

EXAMPLE 4

5,5-Dimethyl-2-(N-methyl-2-pyrrolyl)thiazolidine-4(S)-carboxylic acid 1.09 g (1.0 ml, 10 mmoles) of N-methylpyrrole-2-aldehyde are added to a solution containing 1.5 g (10 mmoles) of D-penicillamine in 100 ml of methanol at room temperature. After 48 hours, the mixture is evaporated to dryness under reduced pressure. The residue is dissolved in hot benzene, clarified with activated carbon and filtered. While cooling, the title product precipitates in a crystalline form in a yield of 1.54 g (67.5%), m.p. 126°–128° C., $[\alpha]_D^{20} = +87.5°$ (c=0.471, dimethylsulphoxide).

Analysis:

(Molecular weight: 240.3): Calculated: N %=11.66; S %=13.34; Found: N %=11.24; S %=13.44.

IR (cm$^{-1}$): 1721 (CO).

$^1$H-NMR ($\delta$, ppm): 1.25 (s, C—CH$_3$); 1.65 (s, C—CH$_3$); 3.38 (b, NH); 3.55 (m, 3H+1H:N—CH$_3$+H$_4$); 5.77 (s, 1H, H$_2$); 5.90 (m, 1H); 6.13 (m, 1H); 6.68 (m, 1H); (pyrrole protons).

EXAMPLE 5

5,5-Dimethyl-2-(3-pyridyl)-thiazolidine-4(S)-carboxylic acid 0.94 ml (1.07 g, 10 mmoles) of pyridine-3-aldehyde is added to a solution containing 1.5 g (10 mmoles) of D-penicillamine in 30 ml of water at room temperature while stirring. After 10 minutes, the title product begins to crystallize. The mixture is stirred for 1 additional hour, the precipitate is filtered, washed with water and dried. The thus-obtained crude product is dissolved in hot water, filtered and cooled down to give the crystalline title compound in a yield of 1.9 g (79.7%), m.p.: 164°–165° C., $[\alpha]_D^{20} = +145°$ (c=0.556, dimethylsulphoxide).

Analysis:

(Molecular weight: 238.304): Calculated: N %=11.75; S %=13.46; Found: N %=11.17; S %=13.69.

IR (cm$^{-1}$): 1714 (CO).

$^1$H-NMR ($\delta$, ppm): 1.35 (s, C—CH$_3$); 1.6 (s, C—CH$_3$); 3.38 (b, NH); 3.38 (b, NH); 3.64 (s, H$_4$, 1H); 5.78 (s, 1H, H$_2$); 7.42 (m; /7, 8/d); 8.0 (d), 8.49 (dd); 8.63 (d) (pyridine protons).

EXAMPLE 6

5,5-Dimethyl-2-(4-pyridyl)-thiazolidine-4(S)-carboxylic acid 4.7 ml (10 mmoles) of pyridine-4-aldehyde dissolved in 21 ml of methanol are dropped to a solution containing 7.5 g (50 mmoles) of D-pencillamine in 45 ml of water while stirring. After stirring for additional 3 hours, the precipitate is filtered and washed with ethanol to give the title compound in a yield of 6.4 g (54.5%). This product is recrystallized with ethanol with the addition of petroleum ether (b.p. 60°–80° C.), m.p.: 149°–151° C., $[\alpha]_D^{20} = +42.7$ (c=1.32, dimethylsulphoxide).

Analysis:

(Molecular weight 238.3): Calculated: N %=11.75, S %=13.46%; Found: N %=12.07, S %=13.63.

IR (cm$^{-1}$): 1722 (CO).

EXAMPLE 7

2-(2-Benzofuryl)-5,5-dimethylthiazolidine-4(S)-carboxylic acid 1.46 g (1.39 ml, 10 mmoles) of 2-formylbenzofuran are added to a solution containing 1.5 g (10 mmoles) of D-penicillamine in 150 ml of methanol while stirring. After 48 hours, the solution is evaporated to dryness under reduced pressure. The syrupic residue is dissolved in hot benzene and filtered. After adding petroleum ether, the title compound is precipitated in a crystalline form with a yield of 1.9 g (68.6%), m.p.: 96° C., $[\alpha]_D^{20} = +215°$ (c=0.511, dimethylsulphoxide).

Analysis:

(Molecular weight: 277.3): Calculated: N %=5.05, S %=11.56; Found: N %=4.90, S %=11.31.

IR (cm$^{-1}$): 1721 (CO).

$^1$H-NMR ($\delta$, ppm): 1.33 (s, C—CH$_3$); 1.66 (s, C—CH$_3$); 3.38 (b, NH/3.75/s, 1H, H$_4$/5.89/s, 1H, H$_2$/; 6.92/d/7.27/m/7.59/m/) (aromatic protons).

EXAMPLE 8

5,5-Dimethyl-2-(5-indanyl)-thiazolidine-4(S)-carboxylic acid 1.44 g (10 mmoles) of 5-formylindane are portionwise added to a solution containing 1.5 g of D-penicillamine in 100 ml of methanol at room temperature while stirring. After 48 hours, the mixture is evaporated to dryness. The residue is dissolved in ether with boiling, treated with activated carbon and filtered. The crude product is precipitated by adding petroleum ether. The thus-obtained product is dissolved in hot ethanol, clarified with carbon, filtered, then water is added up to a beginning opalescence. On cooling, the title compound precipitates in a crystalline form in a yield of 1.57 g (57.1%), m.p. 140°–142° C., $[\alpha]_D^{20} = +18°$ (c=0.551, dimethylsulphoxide).

Analysis:

(Molecular weight: 275.342): Calculated: S %=11.65; Found: S %=11.75.

IR (cm$^{-1}$): 1722 (CO).

$^1$H-NMR (δ, ppm): 1.32 (s, C—CH$_3$); 1.6 (s, C—CH$_3$); 3.88 (b, NH); 3.62 (s, 1H; H$_4$); 5.76 (s, 1H, H$_2$).

EXAMPLE 9

5,5-Dimethyl-2-(3-nitrophenyl)-thiazolidine-4(S)-carboxylic acid magnesium salt

A solution containing 4.48 g (30 mmoles) of D-penicillamine and 4.53 g (30 mmoles) of 3-nitrobenzaldehyde in 90 ml of 30% methanol is stirred for 3 hours. The precipitate is filtered and washed with methanol. The thus-obtained product is recrystallized from methanol by adding water to give the acid in a yield of 7.17 g (84.6%).

2.82 g (10 mmoles) of the title acid are added to a suspension containing 0.22 g (5 mmoles) of magnesium oxide in 30 ml of water and the mixture is heated to 60° C. until the complete dissolution. The clear solution is evaporated to dryness under reduced pressure and dried over phosphorus pentoxide in a desiccator. The title magnesium salt is obtained in a quantitative yield as a syrup.

The title acid melts at 139° to 140° C., $[\alpha]_D^{20} = -26.4°$ (c=0.588, dimethylsulphoxide).

Analysis:

(Molecular weight: 282.3): Calculated: N %=9.92; S %=11.36; Found: N %=9.12, S %=11.02.

IR (cm$^{-1}$): 1726 (CO).

$^1$H-NMR (δ, ppm): 1.36 (s, 3H, CH$_3$); 1.69 (s, 3H, CH$_3$); 3.57 (s, 1H, H-4); 5.76 (s, 1H, H-2); 7.65 (t, 1H); 7.95 (dd, 1H); 8.21 (dd, 1H); 8.39 (s, 1H) (aromatic signals).

The magnesium salt: $[\alpha]_D^{21} = -45°$ (c=0.63, water).

Analysis:

(Molecular weight: 586.8): Calculated: N %=9.55, S %=10.93; Found: N %=9.33, S %=10.99.

EXAMPLE 10

5,5-Dimethyl-2-(4-fluorophenyl)-thiazolidine-4(S)-carboxylic acid and potassium salt 6.31 ml (60 mmoles) of 4-fluorobenzaldehyde dissolved in 40 ml of methanol are added to a solution containing 9.0 g (60 mmoles) of D-penicillamine in 200 ml of water while stirring. After stirring for 3 hours, the precipitate is filtered to give 13.8 g (90%) of a crude product. This is recrystallized from methanol by adding water to give the title acid.

1.0 g of potassium hydrogen carbonate is dissolved in 10 ml of distilled water, 2.55 g (10 mmoles) of the title acid are added to this solution and warmed to 60° C. on a steam bath. The acid dissolves with the liberation of carbon dioxide. The solution obtained is evaporated to a thick syrup and dried to constant weight over phosphorus pentoxide in a desiccator. The title potassium salt is obtained in the form of a hygroscopic powder.

The title acid melts at 126°–127° C., $[\alpha]_D^{25} = +86.9°$ (c=0.473, dimethylsulphoxide).

Analysis:

(Molecular weight: 255.3): Calculated: N %=5.49; S %=12.56; Found: N %=5.56, S %=12.47.

EXAMPLE 11

5,5-Dimethyl-2-(4-methylmercaptophenyl)-thiazolidine-4(S)-carboxylic acid

A solution containing 4.48 g (30 mmoles) of D-penicillamine and 3.99 ml (30 mmoles) of 4-methylmercaptobenzaldehyde in 90 ml of 30% aqueous methanol is stirred for 6 hours. The white solid precipitate is filtered out to give 8.26 g (97.1%) of the title product which can be recrystallized from methanol by adding water, m.p.: 150°–152° C., $[\alpha]_D^{20} = +74.4°$ (c=0.516, dimethylsulphoxide).

Analysis:

(Molecular weight: 283.4): Calculated: N %=4.94, S %=22.63; Found N %=4.85, S %=22.31.

IR (cm$^{-1}$): 2960 and 2914 (CH$_3$), 1720 (CO).

$^1$H-NMR (δ, ppm): 1.30 (s, C—CH$_3$); 1.36 (s, C—CH$_3$); 1.55 (s, C—CH$_3$); 1.65 (s, C—CH$_3$); 2.45 (s, 4'—CH$_3$); 2.48 (s, 4'—CH$_3$); 3.56 (s, H-4); 3.69 (s, H-4); 5.60 (s, H-2); 5.82 (s, H-2); 7.17–7.45 (m, aromatic).

EXAMPLE 12

2-(2-Carboxyphenyl)-5,5-dimethylthiazolidine-4(S)-carboxylic acid

A mixture containing 6 g (30 mmoles) of 2-carboxybenzaldehyde and 6 g (30 mmoles) of D-penicillamine in 44 ml of water is stirred for 3 hours. The precipitate is filtered out and washed with aqueous methanol to given the crude title acid in a yield of 9.86 g (82.6%) which can be recrystallized from methanol containing water, m.p.: 185°–186° C. $[\alpha]_D^{18} = +385°$ (c=0.51, methanol).

Analysis:

(Molecular weight 281.3): Calculated: N %=4.98, S %=11.40; Found: N %=4.96 S %%=11.39.

IR (cm$^{-1}$): 1763 and 1705 (CO).

$^1$H-NMR (δ, ppm): 1.50 (s, 3H, CH$_3$); 1.60 (s, 3H, CH$_3$); 3.41 (b, s, 2H, OH); 4.51 (s, 1H, H-4); 6.45 (s, 1H, H-2); 7.87 (m, 4H, aromatic).

EXAMPLE 13

2-(3,4-Dimethoxy-2-carboxyphenyl)-5,5-dimethyl-thiazolidine-4(S)-carboxylic acid 2.1 g (10 mmoles) of opianic acid are dissolved in 30 ml of hot water and the solution is cooled to about 60° C. After adding 1.5 g (10 mmoles) of D-penicillamine, an oily product separates from the opalescent solution which becomes crystalline after standing overnight. The title acid is obtained in a yield of 2.75 g (80.5%) and can be recrystallized from methanol by adding water, m.p.: 90°–91° C., $[\alpha]_D^{20} = +326°$ (c=0.772, methanol).

Analysis:

(Molecular weight: 341.4): Calculated: N %=4.10, S %=9.39; Found: N %=4.21, S %=9.21.

IR (cm$^{-1}$): 1721 and 1690 (CO).

$^1$H-NMR (δ, ppm): 1.50 (s, 3H, CH$_3$); 1.60 (s, 3H, CH$_3$); 3.50 (br, OH); 3.79 (s, 3H, OCH$_3$); 3.84 (s, 3H, OCH$_3$); 4.43 (s, 1H, H-4); 6.35 (s, 1H, H-2); 7.35 (q, 2H, aromatic).

EXAMPLE 14

5,5-Dimethyl-2-hydroxymethylthiazolidine-4(S)-carboxylic acid.

A solution containing 3.0 g (50 mmoles) of glycolaldehyde and 7.5 g (30 mmoles) of D-penicillamine in 30 ml of 30% methanol is stirred for 6 hours. The precipitate is filtered out and recrystallized from 40 ml of hot water to give the title acid in a yield of 2.17 g (22.7%), m.p.: 179°–180° C., $[\alpha]_D^{24} = +167°$ (c=0.62, 10% sodium hydrogen carbonate solution).

Analysis:

(Molecular weight: 191.2): Calculated: N %=7.32, S %=16.76; Found: N %=7.44, S %=16.78.

IR (cm$^{-1}$): 1635 (CO).

| $^1$H—NMR ($\delta$, ppm): | 1.20 and 1.55 (C—methyl, cis) |
| --- | --- |
| | 3.20 (CH$_2$—A) |
| | 3.41 (CH$_2$—B) |
| | 3.44 (H-4) cis |
| | 4.58 (H-2) |

EXAMPLE 15

2-(3,5-Dibromo-4-hydroxyphenyl)-5,5-dimethyl-thiazolidine-4(S)-carboxylic acid

A solution containing 5.6 g (20 mmoles) of 3,5-dibromo-4-hydroxybenzaldehyde and 3 g (20 mmoles) of D-penicillamine in 100 ml of 30% methanol is stirred for 16 hours. The precipitated product is filtered and washed with aqueous methanol to give 6.77 g (82.3%) of the title acid which can be recrystallized from a mixture containing ethanol, dimethylformamide and water, m.p.: 154°–155° C., $[\alpha]_D^{25} = +87°$ (c=1.362, dimethylsulphoxide).

Analysis:

(Molecular weight: 415.1): Calculated: N %=3.41, S %=7.80, Br %=38.88; Found: N %=3.56, S %=7.77, Br %=38.22.

IR (cm$^{-1}$): 1708 (CO).

$^1$H-NMR ($\delta$, ppm): 1.27 (s, CH$_3$); 1.30 (s, CH$_3$); 1.52 (s, CH$_3$); 1.61 (s, CH$_3$); 3.50 (s, H-4); 3.57 (s, H-4); 5.50 (s, H-2); 5.74 (s, H-2); 3.45 (br, OH); 7.46; 7.70 (aromatic); 9.98 (br, OH).

EXAMPLE 16

5,5-Dimethyl-2-(3-hydroxy-5-hydroxymethyl-2-methyl-4-pyridyl)-thiazolidine-4(S)-carboxylic acid 2.03 g (10 mmoles) of pyridoxal hydrochloride are added to a solution containing 1.50 g (10 mmoles) of D-penicillamine and 0.56 g of potassium hydroxide in 10 ml of water. After stirring for 16 hours, the precipitate is filtered out to give the title acid in a yield of 2.26 g (75.7%) which can be purified by boiling with ethanol, m.p.: 201°–202° C., $[\alpha]_D^{25} = +68.1°$.

Analysis:

(Molecular weight: 298.3): Calculated: N %=9.29; S %=10.74. Found: N %=9.30, S %=10.54.

IR (cm$^{-1}$): 3340 and 3292 (OH), 1725 (CO).

$^1$H-NMR ($\delta$, ppm): 1.66 and 1.83 (C-methyl, trans), 1.71 and 1.91 (C-methyl, cis), 2.83 (aromatic methyl), about 5 (CH$_2$), 6.56 (H-2) (cis), 6.68 (H-4) trans.

EXAMPLE 17

2-(2,4-Dichlorophenyl)-5,5-dimethylthiazolidine-4(S)-carboxylic acid 3.5 g (20 mmoles) of 2,4-dichlorobenzaldehyde dissolved in 17 ml of methanol are added to a solution containing 3.0 g (20 mmoles) of D-penicillamine in 65 ml of water while stirring. After stirring for 16 hours, the precipitate is filtered, washed with 50% methanol and dried to give the title acid in a yield of 5.82 g (95%), m.p.: 150°–151° C., $[\alpha]_D^{20} = +353°$ (c=0.45, dimethylsulphoxide).

Analysis:

(Molecular weight: 306.2): Calculated: Cl %=23.16, S %=10.47; Found: Cl %=22.79, S %=10.60.

IR (cm$^{-1}$): 1700 (CO).

$^1$H-NMR ($\delta$, ppm): 1.30 and 1.50 (C-methyl, cis), 3.35 (NH), 3.71 (H-4, cis), 5.88 (H-2, cis).

EXAMPLE 18

5,5-Dimethyl-2-(4-methylphenyl)-thiazolidine-4(S)-carboxylic acid

A solution containing 1.50 g (10 mmoles) of D-penicillamine and 1.18 ml (10 mmoles) of 4-methylbenzaldehyde in 30 ml of 30% methanol is stirred for 1 hour. The precipitated crystals are filtered out and washed with 30% methanol to give the crude title acid in a yield of 2.25 g (89.5%) which can be recrystallized from methanol by adding water, m.p.: 89°–90° C., $[\alpha]_D = +53.5$ (c=0.784, dimethylsulphoxide).

Analysis:

(Molecular weight: 251.3): Calculated: N %=5.57, S %=12.76; Found: N %=5.51, S %=12.11.

IR (cm$^{-1}$): 1740 (CO).

$^1$H-NMR ($\delta$, ppm): 1.26 and 1.54 (C-methyl, cis), 1.36 and 1.69 (C-methyl, trans), 2.28 (aromatic methyl), 3.58 (H-4) cis, 5.81 (H-2) cis, 3.64 (H-4) trans, 5.58 (H-2) trans.

EXAMPLE 19

5,5-Dimethyl-2-(4-hydroxyphenyl)-thiazolidine-4(S)-carboxylic acid 1.26 g (10 mmoles) of 4-hydroxybenzaldehyde dissolved in 20 ml of 30% aqueous methanol are added to a solution containing 1.49 g (10 mmoles) of D-penicillamine in 30 ml of 30% methanol. After stirring for 20 hours and recrystallization from ethanol containing water, the title acid is obtained in a yield of 2.4 g (94.8%), m.p.: 207°–209° C., $[\alpha]_D = +91.3°$ (c=0.2, dimethylformamide).

Analysis:

(Molecular weight: 253.2): Calculated: N %=5.53, S %=12.64; Found: N %=5.43, S %=12.60.

IR (cm$^{-1}$): 1630, 1608, 1589 (CO).

$^1$H-NMR ($\delta$, ppm): 1.32 and 1.57 (C-methyl, cis), 1.34 and 1.66 (C-methyl, trans), 2.71 (OH, cis), 2.88 (OH, trans), 3.56 (H-4) cis, 5.76 (H-2) cis, 3.62 (H-4) trans, 5.55 (H-2) trans.

EXAMPLE 20

5,5-Dimethyl-2-(2-hydroxyphenyl)-thiazolidine-4(S)-carboxylic acid

A solution containing 4.5 g (30 mmoles) of D-penicillamine and 3.16 ml (30 mmoles) of salicylaldehyde in 90 ml of 30% methanol is stirred for 3 hours. The precipitated product is filtered out, washed with 50% methanol and dried to give the title acid in a yield of 7.05 g (92.7%) which is recrystallized from methanol, m.p. 179°–181° C., $[\alpha]_D = 129.8°$ (c=0.48, dimethylformamide).

Analysis:

(Molecular weight: 253.2): Calculated: N %=5.53, S %=12.64; Found: N %=5.36, S %=12.25.

IR (cm$^{-1}$): 1638.

$^1$H-NMR (δ, ppm): 1.30 and 1.48 (C-methyl, cis), 1.36 and 1.69 (C-methyl, trans), 3.16 (OH), 3.64 (H-4) trans, 5.76 (H-2) trans, 5.67 (H-4) cis, 5.90 (H-2) cis.

EXAMPLE 21

3-Acetyl-5,5-dimethyl-2(R)-(4-fluorophenyl)-thiazolidine-4(S)-carboxylic acid

A solution containing 5.74 g (30 mmoles) of N-acetyl-D-penicillamine and 3.2 ml of 4-fluorobenzaldehyde in 20 ml of ether saturated with gaseous hydrogen chloride is stirred. After 5 to 6 minutes an oil separates which becomes crystalline after 30 minutes on rubbing. The precipitate is filtered out and washed with ether to give the title acid in a yield of 7.81 g (87.1%) which can be recrystallized from ethyl acetate, m.p. 144°–146° C., $[α]_D^{20} = +206.9°$.

Analysis:

(Molecular weight: 297.3): Calculated: N %=4.71, S %=10.78; Found: N %=4.80, S %=11.12.

IR (cm$^{-1}$): 1742 (CO).

$^1$H-NMR (δ, ppm): 1.60 (s, 3H, CH$_3$); 1.45 (s, 3H, CH$_3$); 1.83 (s, 3H, NHCOCH$_3$); 4.71 (s, 1H, H-4); 6.32 (s, 1H, H-2); 7.05–7.35 (multiplet, 4H, aromatic).

EXAMPLE 22

3-Acetyl-2(R)-(4-chlorophenyl)-5,5-dimethylthiazolidine-4(S)-carboxylic acid 4.2 g (30 mmoles) of 4-chlorobenzaldehyde are given to the suspension containing 5.73 g (30 mmoles) of N-acetyl-D-penicillamine in 18 ml of ethereal hydrogen chloride solution under stirring for 12 minutes. After dissolution, a product is precipitated which is filtered out and washed with ether to give 8.32 g (88.4%) of the title compound, m.p.: 197°–198° C. after recrystallization from ethyl acetate, $[α]_D = +230.5°$ (c=0.59, methanol).

Analysis:

(molecular weight: 313.8): Calculated: N %=4.46, S %=10.22, Cl %=11.30, Found: N %=4.41, S %=10.18, Cl %=11.11.

IR (cm$^{-1}$): 1742 (CO).

$^1$H-NMR (δ, ppm): 1.45 (s, 3H, CH$_3$); 1.59 (s, 3H, CH$_3$); 1.85 (s, 3H, NHCOCH$_3$); 4.71 (s, 1H, 4-H); 6.32 (s, 1H, 2-H); 7.33 (multiplet, 4H, aromatic).

EXAMPLE 23

3-Acetyl-2(S)-(4-chlorophenyl)-5,5-dimethylthiazolidine-4(S)-carboxylic acid 5.6 ml of acetic anhydride are given to a suspension containing 2.71 g (10 mmoles) of 2-(4-chlorophenyl)-5,5-dimethylthiazolidine-4(S)-carboxylic acid in 5.6 ml of hot water and the mixture is kept at 100° C. for 8 minutes. A complete solution is obtained. On cooling, the product precipitates to give the title compound in a yield of 2.39 g (76.1%) which is recrystallized from ethanol by adding water, m.p.: 203°–205° C., $[α]_D^{22} = +111.5°$ (c=1.44, dimethylsulphoxide).

Analysis:

(Molecular weight: 319.8): Calculated: Cl %=11.30, S %=10.22; Found: CCl %=11.94, S %=9.97.

IR (cm$^{-1}$): 1730 (CO), 1626 (amide).

$^1$H-NMR (δ, ppm): 1.36 (s, 3H, CH$_3$); 1.61 (2, 3H, CH$_3$); 1.86 (N—COCH$_3$); 4.60 (s, 1H, H-4); 6.27 (s, 1H, H-2); 7.33 (s, 2H, H-3′, 5′); 7.76 (s, 2H, H-2′, 6′).

EXAMPLE 24

2(S)-(2-Acetoxyphenyl)-3-acetyl-5,5-dimethylthiazolidine-4(S)-carboxylic acid

A solution containing 1.0 g of 5,5-dimethyl-2-(2-hydroxyphenyl)-thiazolidine-4(S)-carboxylic acid in 7 ml of pyridine and 3 ml of acetic anhydride is kept for 20 hours, then the mixture is evaporated and three times 20 ml of toluene each are distilled from the residue. The remained crystalline material is recrystallized from the mixture of acetone and petroleum ether to give the title compound in a yield of 0.9 g (67.5 %), m.p.: 214°–216° C. $[α]_D^{22} = +34$ (c=0.47, chloroform).

Analysis:

(Molecular weight: 337.18): Calculated: N %=4.13, S %=9.40; Found: N %=4.00, S %=9.33.

IR (cm$^{-1}$): 1778 and 1760 (CO), 1614 (amide).

$^1$H-NMR (δ, ppm): 1.28 and 1.58 (C-methyl), 1.73 N—COCH$_3$, 2.29 O—COCH$_3$, 3.36 (NH), 4.47 (H-4), 6.34 (H-2)

EXAMPLE 25

3-Acetyl-2(S)-(2,4-dichlorophenyl)-5,5-dimethyl-thiazolidine-4(S)-carboxylic acid 5.56 ml of acetic anhydride are given to a hot suspension containing 2-(2,4-dichlorophenyl)-5,5-dimethyl-thiazolidine-4(S)-carboxylic acid in 5.56 ml of water. The mixture is heated at 100° C. for 6 minutes, then cooled down and diluted with 10 ml of water. The crystalline precipitate is filtered to give the title compound in a yield of 2.57 g (73.8%). After recrystallization from a mixture of methanol and water, this acid melts at 233°–235° C., $[α]_d^{22} = -142$.

Analysis:

(Molecular weight: 350.08): Calculated: S %=9.20; Found: S %=9.08.

IR (cm$^{-1}$): 1738 (CO).

$^1$H-NMR (δ, ppm): 1.27 (s, CH$_3$); 1.37 (s, CH$_3$), 1.56 (s, CH$_3$), 1.60 (s, CH$_3$); 2.02 (N—COCH$_3$); 4.49 (s, H-4); 4.78 (s, H-4); 6.27 (s, H-2); 6.44 (s, H-2); 7.60–8.00 (multiplet, 3H, aromatic).

EXAMPLE 26

3-Acetyl-5,5-dimethyl-2(S)-(4-methylphenyl)-thiazolidine-4(S)-carboxylic acid 5.6 ml of acetic anhydride are added to a hot suspension containing 2.51 g (10 mmoles) of 5,5-dimethyl-2-(4-methylphenyl)-thiazolidine-4(S)-carboxylic acid in 5.6 ml of water, then the mixture is heated at 100° C. for 5 minutes. On cooling, crystals are precipitated which are recrystallized from isopropanol to give the title compound in a yield of 2.15 g (73.3%), m.p.: 214°218° C., $[α]_D^{19} = -101°$ (c=0.71, methanol).

Analysis:

(Molecular weight: 293.3): Calculated: N % =4.77, S %=10.93; Found: N %=4.66, S %=10.91.

IR (cm$^{-1}$): 1732 (CO).

$^1$H-NMR (δ, ppm): 1.35 (s, 3H, CH$_3$); 1.59 (s, 3H, CH$_3$); 1.81 (s, 3H, NHCOCH$_3$); 2.30 (s, 3H, aromatic methyl); 4.58 (s, 1H, H-4); 6.23 (s, 1H, H-2); 7.14–7.63 (multiplet, 4H, aromatic).

EXAMPLE 27

3-Acetyl-5,5-dimethyl-2(S)-phenylthiazolidine-4(S)-carboxylic acid 0.47 g (2 mmoles) of 5,5-dimethyl-2(S)-phenylthiazolidine-4(S)-carboxylic acid is suspended in 5 ml of pyridine while stirring. The temperature of the suspension is adjusted to 5° C. by cooling with ice-water and 0.17 g of acetyl chloride is dropped in. The mixture is stirred for 1 additional hour, then poured in 60 ml of ice-cold 2N sulphuric acid. After several hours, the precipitated product is filtered out, washed with water and dried. The product is dissolved in ethanol and water is added to precipitate the title compound in a yield of 0.38 g (70.3%), m.p.: 216°–217° C., $[\alpha]_D^{20} = -109°$ (c=0.686, methanol).

Analysis:

Molecular weight: 270.3): Calculated: N %−5.18, S %=11.48; Found: N %=5.30, S %=11.27.

IR (cm$^{-1}$): 1732 (CO), 1621 (amide).

$^1$H-NMR (δ, ppm): 1.37 (s, 3H, CH$_3$); 1.62 (s, 3H, CH$_3$); 1.85 (s, 3H, NHCOCH$_3$); 4.60 (s, 1H, H-4); 6.24 (s, 1H, H-2); 7.30–7.75 (multiplet, 5H, aromatic).

EXAMPLE 28

2(S)-(4-Acetoxyphenyl)-3-acetyl-5,5-dimethylthiazolidine-4(S)-carboxylic acid A solution containing 1.5 g of 5,5-dimethyl-2-(4-hydroxyphenyl)-thiazolidine-4(S)-carboxylic acid in the mixture of 15 ml of pyridine and 3 ml of acetic anhydride is kept for 20 hours and then evaporated. From the residue, twice 30 ml of toluene each are distilled off, whereupon the residue is recrystallized from a mixture of acetone and petroleum ether to give the title compound in a yield of 1.5 g (75%), m.p.: 199°–201° C., $[\alpha]_D^{22} = -61.7°$ (c=0.52, chloroform).

Analysis:

Molecular weight: 337.18): Calculated: N %=4.12; S %=9.43; Found: N %=4.15, S %=9.42.

IR (cm$^{-1}$): 1734–1770 (CO).

$^1$H-NMR (δ, ppm): 1.30 and 1.51 (C-methyl), 2.27 (NCOCH$_3$), 3.36 (OH), 4.55 (H-4), 6.45 (H-2).

EXAMPLE 29

3-Acetyl-5,5-dimethyl-2(S)-(4-fluorophenyl)-thiazolidine-4(S)-carboxylic acid 11.2 ml of acetic anhydride are portion-wise added to a suspension containing 5.1 g (20 mmoles) of 5,5-dimethyl-2-(4-fluorophenyl)-thiazolidine-4(S)-carboxylic acid in 11.2 ml of hot water. The mixture is heated at 100° C. for 5 minutes, then cooled down. The crystals are filtered out to give the title compound in a yield of 5.83 g (98%) which is recrystallized from the mixture of ethanol and ether, m.p.: 193.5° C., $[\alpha]_D^{22} = -96.8°$ (c=0.62, methanol).

Analysis:

(Molecular weight: 297.3): Calculated: N %=4.71, S %=10.78; Found: N %=4.63, S %=10.85.

IR (cm$^{-1}$): 1736 (CO), 1626 (amide).

$^1$H-NMR (δ, ppm): 1.37 (C—CH$_3$, s, 3H); 1.62 (C—CH$_3$, s, 3H); 1.86 (N—COCH$_3$); 4.60 (H-4, s, 1H); 6.24 (H-2, s, 1H); 7.05 (H'-3, H'-5, s, 2H); 7.80 (H'-2, H'-6, s, 2H).

EXAMPLE 30

3-Acetyl-5,5-dimethyl-2(S)-(5-nitro-2-furyl)-thiazolidine-4(S)-carboxylic acid A solution containing 2.72 g (10 mmoles) of 5,5-dimethyl-2-(5-nitro-2-furyl)-thiazolidine-4(S)-carboxylic acid in 5.6 ml of water is heated to 100° C. on the steam bath. After adding 5.6 ml of acetic anhydride, the mixture is heated for additional 3 minutes. On the addition of water, 2.6 g (84.3%) of the title compound are precipitated, m.p.: 191°14 194° C., $[\alpha]_D^{25} = -315.8°$ (c=0.938, dimethylsulphoxide).

[5,5-dimethyl-2-(5-nitro-2-furyl)-thiazolidine-4(S)-carboxylic acid used as starting material was prepared as described in Example 1.]

Analysis:

(Molecular weight: 308.3): Calculated: N %=9.08, S %=10.40; Found: N %=8.72, S %=10.13.

IR (cm$^{-1}$): 1740 (CO).

$^1$H-NMR (δ, ppm): 1.30 and 1.41 (CH$_3$); 1.57 and 1.61 (CH$_3$); 2.03 (NHCOCH$_3$); 3.45 (OH); 4.50 and 4.79 (H-4); 6.37 and 6.71 (H-2); 6.95; 7.16; 7.71 and 7.76 (aromatic).

EXAMPLE 31

3-[2-(4-Chlorophenoxy)-isobutyryl]-5,5-dimethyl-2(S)-phenylthiazolidine-4(S)-carboxylic acid 1.17 g (5 mmoles) of 5,5-dimethyl-2-phenylthiazolidine-4(S)-carboxylic acid and 0.7 ml of triethylamine are dissolved in 20 ml of dichloromethane while stirring and the solution is cooled to 0° C. Then, 2-(4-chlorophenoxy)-isobutyryl chloride dissolved in 4 ml of dichloromethane is added under stirring. After stirring for 3 hours, the solution is washed with water, dried over anhydrous magnesium sulphate and evaporated. The obtained syrup is recrystallized from methanol by adding water to give the title compound in a yield of 1.39 g (64%), m.p.: 177°–181° C., $[\alpha]_D^{21} = 0°$ (c=0.94, dimethylsulphoxide).

Analysis:

(Molecular weight: 433.9): Calculated: N %=3.23, S %=7.39, Cl %=8.17; Found: N %=3.11, S %=7.68, Cl %=8.14.

IR (cm$^{-1}$): 3017 and 2975 (CH$_3$), 1740 (CO), 1609 (amide-II).

$^1$H-NMR (δ, ppm): 1.32; 1.39; 1.44 and 1.55 (4x3s, CH$_3$); 5.04 (s, 1H, H-4); 6.26 (s, 1H, H-2); 6.76–7.36 (multiplet, 9H, aromatic).

EXAMPLE 32

Methyl 5,5-dimethyl-2(S)-(5-nitrofuryl)-thiazolidine-4(S)-carboxylate

An ethereal diazomethane solution prepared from 4.45 g (43.2 mmoles) of nitrosomethylurea is portion-wise added under cooling to the solution containing 2.72 g (10 mmoles) of 5,5-dimethyl-2-(5-nitrofuryl)-thiazolidine-4(S)-carboxylic acid in 50 ml of methanol until the yellow colour becomes stable. After about 1 hour, the excess of diazomethane is decomposed by adding a few drops of acetic acid. [5,5-Dimethyl-2-(5-nitrofuryl)-thiazolidine-4(S)-carboxylic acid was prepared as described in Example 1.] After evaporating the solvent, the product is obtained as a light yellow syrup, $[\alpha]_D^{24} = 194°$ (c=0.670, chloroform).

MS=286 (M$^+$).

IR (cm$^{-1}$): 1743 (CO) (KBr).

$^1$H—NMR (δ, ppm): 1.3 (3H, C—CH$_3$); 1.68 (3H, C—CH$_3$); 3.8 (4H, H$_4$+O—CH$_3$); 5.7 (1H, H$_2$); 6.63/1H H$_3$ and H$_4$ 7.26/1H

EXAMPLE 33

Preparation of dragées containing a thiazolidine-4(S)-carboxylic acid derivative as active ingredient The active ingredient is homogenized together with the additive materials of the inner phase of the tablet, granulated, dried and then compressed to tablets in a manner known in se. From the thus-obtained tablets, dragées, covered with a sugar coat are prepared by using the suspension process.

| Composition | mg |
| --- | --- |
| Active ingredient | 100 |
| Potatoe starch | 30 |
| Lactose | 50 |
| White gelatine | 10 |
| Carboxymethylcellulose sodium | 1 |
| Polyvidone | 2 |
| Talc | 36 |
| Magnesium stearate | 4 |
| Colloidal silicon dioxide | 3 |
| Titanium dioxide | 1 |
| Iron oxide pigment | 2 |
| Saccharose | 106 |
| Calcium carbonate | 55 |

EXAMPLE 45

Preparation of dragées containing a thiazolidine-4(S)-carboxylic acid derivative as active ingredient The active ingredient is homogenized together with the tablet additives and tablets containing 200 mg of the active ingredient each are compressed from the homogenized mixture. From the thus-obtained tablets, film-coated dragées are prepared.

| Composition | mg |
| --- | --- |
| Active ingredient | 100 |
| Lactose | 21.6 |
| Carboxymethylcellulose sodium | 15 |
| Microcrystalline cellulose | 100 |
| Talc | 11 |
| Magnesium stearate | 4 |
| Colloidal silicon dioxide | 2 |
| Methacrylic acid acrylic ester polymer | 0.3 |
| Titanium dioxide | 3 |
| Iron oxide pigment | 0.1 |

The compounds prepared were subjected to acute toxicity investigations. For this purpose, the compounds under test were dissolved in an aqueous sodium carbonate solution and administered intraperitoneally (i.p.) or intravenously (i.v.) to the animals (40 days old CFLP female mice).

Some characteristic LD$_{50}$ values of the compounds of the invention are as follows:

| Compound of the Example | LD$_{50}$ mg/kg of body-weight |
| --- | --- |
| 1 | 2191 (i.v.) |
| 14 | 5000 (i.p.) |
| 30 | 2500 (i.p.) |
| 27 | 1500 (i.p.) |
| 22 | 550 (i.p.) |

It is obvious that the LD$_{50}$ values are sufficiently high as to permit the therapeutical use of these compounds.

In order to investigate the liver protecting effect, the compounds were tested at CFY male rats with 200 to 240 g of body-weight after a starvation for 18 hours.

An experimental liver damage was elicited by using carbon tetrachloride, allyl alcohol or galactosamine. The activity of the serum glutamate-oxalacetate-transaminase (SGOT), the triglyceride (TG) content of the liver as well as the histological picture of the liver were studied.

Liver damaging agents (1.5 g/kg of body-weight of carbon tetrachloride orally; 0.75 g/kg of body-weight of galactosamine intraperitoneally) were administered to the starved animals, whereupon the animals received the compound under test in a dose of 100 mg/kg of body-weight intraperitoneally after 6 hours.

(a) The results of the carbon tetrachloride intoxication followed by treatment with the compounds under test are as follows:

| Compound of the Example No. | SGOT activity (unit/liter) | TG mg/mg of protein |
| --- | --- | --- |
| Control | 81.7 ± 16 | 40 ± 8 |
| Carbon tetrachloride (CCl$_4$) | 269.0 ± 14 | 86 ± 17 |
| CCl$_4$ + 1 | 224.0 ± 14 | 51 ± 15 |
| CCl$_4$ + 2 | 229.0 ± 14 | 84 ± 6 |
| CCl$_4$ + 5 | 243.0 ± 21 | 61 ± 14 |
| CCl$_4$ + 7 | 224.0 ± 14 | 61 ± 13 |
| CCl$_4$ + 8 | 234.0 ± 23 | 76 ± 10 |
| CCl$_4$ + 10 | 227.0 ± 40 | 81 ± 11 |
| CCl$_4$ + 6 | 250.0 ± 13 | 88 ± 20 |
| CCl$_4$ + 11 | 235.0 ± 19 | 70 ± 14 |
| CCl$_4$ + 9 | 232.0 ± 34 | 83 ± 19 |
| CCl$_4$ + 4 | 241.0 ± 21 | 114 ± 24 |
| CCl$_4$ + catergen* | 241.0 ± 23 | 77 ± 7 |

*catergen is a known liver protecting agent, chemically (+)-2-(3,4-dihydroxyphenyl)-3,5,7-chromanetriol As a consequence of the damage of liver tissue, the SGOT level was increased to its 3.3-fold in the group treated with only carbon tetrachloride which was due to the appearance of the intracellular glutamate-oxalacetate-transaminase in the serum. Simultaneously, the liver triglyceride content of the same group was increased to the 2.14-fold. These alterations are in accordance with the degree of the necrotic changes observed on the histological sections. On administration of the compounds of the invention, the SCOT activity is diminished according to the data shown in the Table.

(b) The results of the allyl alcohol intoxication followed by treatment with the compounds under test are as follows:

After 24 hours, the animals were killed and the activity of the serum glutamate-pyruvate-transaminase (SGPT) was determined. After a treatment with allyl alcohol, the SGPT level was increased from a value of 1.81±0.43 μmoles/ml.h. to 4.16±1.63 μmoles/ml. h. This increase was diminished to 2.84±0.97 μmoles/ml.h. by a treatment with a 100 mg/kg of bodyweight dose of the compound described in Example 1.

(c) The result of the galactosamine damage followed by treatment with the compounds under test:

By administering galactosamine, focal necroses surrounded by inflammatory elements as well as fatty tissue degenerative alterations can be caused in the liver. The compounds under test were intraperitoneally given to the animals by 6 hours following the galactosamine intoxication.

Both the number of focally appearing parenchymal necroses as well as the severity of the alterations characteristic of the galactosamine hepatitis were diminished by treatment with the compounds described in Examples 1 and 2.

We claim:

1. A method for treating liver diseases of the type chronic aggressive hepatitis, alcoholic hepatitis, acute hepatic failure, or human liver cirrhosis, which comprises administering to a mammal in need thereof an effective amount of a thiazolidine-4(S)-carboxylic acid derivative of the formula

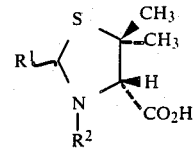

wherein $R^1$ is phenyl or a heterocyclic group selected from the group consisting of is furyl, pyrrolyl, thienyl, benzofuryl, benzopyrrolyl, benzothienyl, pyridyl, quinolinyl, isoquinolinyl, or indanyl substituted with halogen, $C_{1-4}$ alkyl or alkoxy, nitro, mercapto, amino, hydroxyl, carbonyl, $C_{1-4}$ acyl, or acyloxy; and $R^2$ is hydrogen, $C_{1-4}$ alkyl or $C_{1-4}$ alkanoyl; or a pharmaceutically acceptable salt thereof.

* * * * *